United States Patent
Li et al.

(10) Patent No.: US 11,612,558 B2
(45) Date of Patent: Mar. 28, 2023

(54) METHODS OF EXTRACTING MATERIALS FROM PLANT MATERIAL

(71) Applicants: Ping Li, Beijing (CN); Ping Li, Beijing (CN); Qianhua Piao, Beijing (CN); Xiao Lai Chen, Markham (CA)

(72) Inventors: Ping Li, Beijing (CN); Ping Li, Beijing (CN); Qianhua Piao, Beijing (CN); Xiao Lai Chen, Markham (CA)

(*) Notice: Subject to any disclaimer, the term of this patent is extended or adjusted under 35 U.S.C. 154(b) by 176 days.

(21) Appl. No.: 16/891,578

(22) Filed: Jun. 3, 2020

(65) Prior Publication Data

US 2020/0375886 A1   Dec. 3, 2020

Related U.S. Application Data (60) Provisional application No. 62/856,423, filed on Jun. 3, 2019.

(51) Int. Cl.
| | |
|---|---|
| *A61K 36/00* | (2006.01) |
| *A61K 8/9789* | (2017.01) |
| *A23L 33/105* | (2016.01) |
| *B01D 11/02* | (2006.01) |

(52) U.S. Cl.
CPC .......... *A61K 8/9789* (2017.08); *A23L 33/105* (2016.08); *B01D 11/02* (2013.01); *A23V 2002/00* (2013.01)

(58) Field of Classification Search
CPC .................................. B01D 3/10; B01D 5/006
See application file for complete search history.

(56) References Cited

U.S. PATENT DOCUMENTS

2018/0214790 A1* 8/2018 Tucker .................... B01D 3/40

FOREIGN PATENT DOCUMENTS

| CN | 107469402 A | * 12/2017 | ......... B01D 11/0257 |
| KR | 2002072322 A | * 9/2002 | ........... A23L 33/105 |
| KR | 20180004695 A | * 1/2018 | |

* cited by examiner

*Primary Examiner* — Qiuwen Mi (74) *Attorney, Agent, or Firm* — Michael Downs; Downs IP Law LLC (57) ABSTRACT

This invention provides methods for extracting ingredients and materials from plant material, including extracting ingredients from *cannabis* plant material.

7 Claims, 7 Drawing Sheets

METHODS OF EXTRACTING MATERIALS FROM PLANT MATERIAL

This application claims priority from United States provisional patent application No. 62/856,423, filed Jun. 3, 2019, which is incorporated by reference in this application.

TECHNICAL FIELD

This application generally relates to the field of material extraction from plant material, including to methods for extracting active ingredients from plant material.

BACKGROUND

A variety of extraction methods exist for extracting materials from plants. For example, some well-known methods for extracting active ingredients from *cannabis* plant material using solvents include supercritical carbon dioxide extraction and butane honey oil extraction. Solvent-less methods for extraction of active ingredients from *cannabis* are well-known as well, such as those involving pressing the *cannabis* plant material, and drying the *cannabis* plant material and then shaking the dried plant material against a screen or mesh (also known as a dry-sieve extraction).

Many of the known technologies for extracting active ingredients from *cannabis* have disadvantages or shortcomings associated therewith. For example, many of the methods currently used involve first drying the *cannabis* plant material before employing the desired extraction method. Drying the *cannabis* plant can cause certain components of the *cannabis* plant to be lost during the drying process, which components are thus not available to subsequently be extracted by the chosen extraction method. Using solvents in the extraction process likewise can have disadvantages, including the presence of chemical residual products in the final resulting product of the extraction. The use of solvents can also result in the impure extraction of components of the plant material and low extraction rate of single components. Another disadvantage of certain known methods is that impurities or unwanted chemicals may remain in the end product. For example, if plant material has been treated with pesticides or fertilizer, those chemicals may remain in the finished product if certain traditional extraction methods, such as pressing, for example, are used.

There exists a need for extraction methods which are simple and convenient, which extract high concentration, stable materials from plant material, and which minimize or avoid the disadvantages or shortcomings with methods currently used in extraction of plant materials. Therefore, the present invention proposes the following technical solutions.

SUMMARY OF THE INVENTION

According to a first broad aspect of the invention, there is provided a method for extracting chemicals from plant material, such method comprising the following steps: heating a plant material within an apparatus in which a vacuum pressure can be applied on the plant material within the apparatus; cooling an upper surface of the apparatus such that evaporate produced from the plant material being heated is cooled and condenses on such upper surface; and collecting the condensed evaporate from the plant material from such upper surface.

According to another aspect of the invention, there is provided a method according to the above paragraph, wherein the plant material is treated before being placed within the apparatus, such treatment comprising washing the plant material with water.

According to another aspect of the invention, there is provided a method according to one or more of the above paragraphs, wherein the plant material is pasteurized prior to being placed within the apparatus.

According to another aspect of the invention, there is provided a method according to one or more of the above paragraphs, wherein the space within the apparatus into which plant material is placed is cleaned and disinfected prior to the plant material being placed therein.

According to another aspect of the invention, there is provided a method according to one or more of the above paragraphs, wherein the negative vacuum pressure on the plant material within the apparatus is within the range of 650 to 750 Torr.

According to another aspect of the invention, there is provided a method according to one or more of the above paragraphs, wherein the cooling is applied within 3 to 5 hours after the heating of the plant material has commenced.

According to another aspect of the invention, there is provided a method according to one or more of the above paragraphs, wherein the plant material is heated for a period of time between 36 and 50 hours in length.

According to another aspect of the invention, there is provided a method according to one or more of the above paragraphs, wherein the plant material is heated for a first period of time between 18 and 25 hours in length at a temperature between 210° C. and 230° C., and is then heated for a second period of time between 18 and 25 hours in length at a temperature between 170° C. and 190° C.

According to another aspect of the invention, there is provided a method for extracting chemicals from plant material, such method comprising the following steps: heating a plant material within an apparatus in which a vacuum pressure can be applied on the plant material within the apparatus; cooling the apparatus such that evaporate produced from the heated plant material is cooled and condenses; and collecting the condensed evaporate from the plant material.

According to another aspect of the invention, there is provided a method according to one or more of the above paragraphs, wherein the vacuum pressure is applied after heating the plant material.

According to another aspect of the invention, there is provided a method according to one or more of the above paragraphs, wherein the vacuum pressure is maintained continually.

According to another aspect of the invention, there is provided a method according to one or more of the above paragraphs, wherein the vacuum pressure is applied intermittently.

According to another aspect of the invention, there is provided a method according to one or more of the above paragraphs, wherein the cooling is applied within 3 to 5 hours after heating the plant material has commenced.

According to another aspect of the invention, there is provided a method according to one or more of the above paragraphs, wherein the cooling is applied continually after the heating of the plant material has ended.

According to another aspect of the invention, there is provided a method according to one or more of the above paragraphs, wherein the cooling is applied intermittently after the heating of the plant material.

According to another aspect of the invention, there is provided a method according to one or more of the above paragraphs, wherein the plant material is heated for a period of time between 19 and 22 hours in length.

According to another aspect of the invention, there is provided a method according to one or more of the above paragraphs, wherein the plant material is cooled for a period of 27 hours after heating.

According to another aspect of the invention, there is provided a method according to one or more of the above paragraphs, wherein the plant material is selected from one or more plants from the plant genus *Cannabis*. References to "*cannabis*" herein may be understood to refer to one or more plants from the plant genus *Cannabis*. The method of the invention may be used with one or more of *Cannabis sativa*, *Cannabis indica*, and *Cannabis ruderalis*, for example.

BRIEF DESCRIPTION OF THE DRAWINGS

The invention will now be described with reference to the following drawings, wherein like referenced numerals refer to the same item.

DETAILED DESCRIPTION

Figure 1:
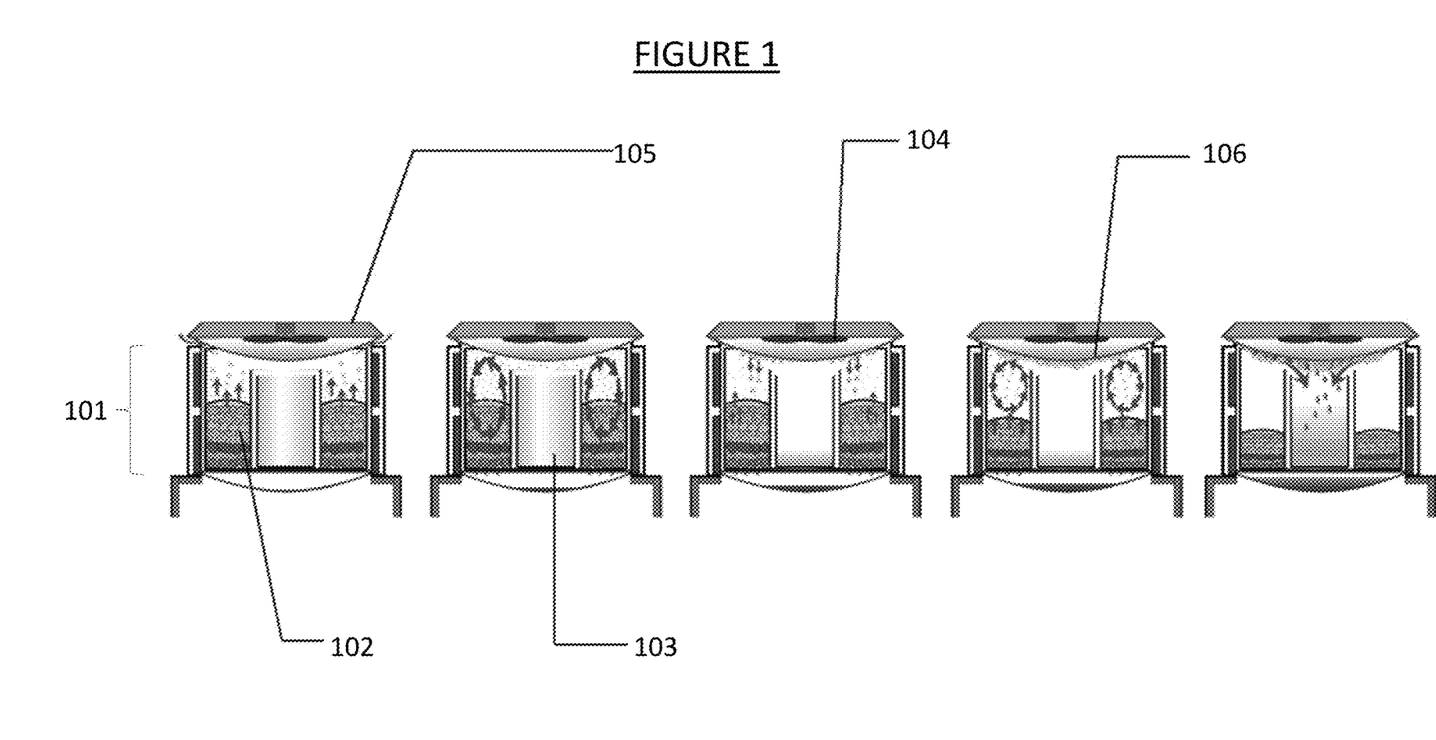
FIG. 1 is a schematic diagram showing a method of extraction of ingredients from plant material in one embodiment of the invention.

FIG. 1 is a schematic diagram showing the steps of a method according to one or more embodiments of the present invention. Many of the steps of the method of FIG. 1 may require the use of an extraction apparatus, represented in FIG. 1 as 101. It will be appreciated to those skilled in the art that, while the apparatus 101 has been depicted as shown in the drawings and as described herein, this is only a schematic diagram meant to be representative of an apparatus that could be used in conjunction with the method of the invention. It will be appreciated by those of skill in the art that changes to the design and appearance of the apparatus can be made while still allowing the method of the invention to be practised substantially as described herein.

According to one embodiment of the method of the invention, raw plant material 102 is placed in a compartment within apparatus 101. Optionally, the raw plant material 102 may be washed with water, or otherwise cleaned, before being placed within apparatus 101. In addition, optionally, the plant material 102 may be pasteurized before being placed within apparatus 101. Pretreatment of the raw plant material such as, but not limited to, that described herein, may be used to remove impurities, such as dust, for example. In one embodiment, the compartment in which the plant material 102 is placed may surround collection compartment 103, as shown in cross-section in FIG. 1, for example.

While this embodiment of the method of the invention describes using raw, undried plant material, it will be appreciated by those skilled in the art that dried plant material could also be used in the method of the invention. It will also be appreciated that plant materials that have been subject to other types of processing could also be used in the method of the present invention.

In one embodiment of this invention, the plant material to be used is *cannabis*. It will be appreciated that other types of plant material may also be used in the method of the present invention. In one embodiment, the amount of *cannabis* plant material in the compartment may be in an amount in the range of 4-5 kg of fresh undried *cannabis* plant. It will be appreciated that other amounts of plant material may be used, depending on the size of apparatus being used, the vacuum compartment size, and the heating and cooling sources.

In one embodiment, the apparatus 101 may be optionally cleaned prior to commencing the method of the invention. Such cleaning may be by industry standard methods, for example, and may include washing with water or other chemicals, ultraviolet treatment, and/or other methods of cleaning and/or disinfecting.

In one embodiment of the method of the invention, the plant material 102 is first placed into an apparatus 101. One embodiment of the method of the invention comprises heating the plant material in one region of a compartment in apparatus 101, while cooling another region of the same compartment in which the plant material has been placed. In one embodiment, the method also comprises applying a vacuum negative pressure to this same compartment. In one embodiment, the compartment into which the plant material is placed has one or more valves designed to allow air to flow in to or out of the compartment. These one or more valves may be operable to be sealed or unsealed, which may be a useful feature both for creating the vacuum negative pressure of the method and for allowing air to flow in to and out of the compartment, if desired. These valves may be operable manually, remotely, mechanically, electronically, or by other means that will be apparent to one of skill in the art.

In one embodiment, after the plant material is placed into the compartment, the one or more valves are closed, creating an airtight seal, and heating the plant material may begin. It will be appreciated to one of skill in the art that it may be advantageous to close the one or more valves after heating of the plant material has commenced, or to optionally open or close the one or more valves at various times during the heating process.

By applying heat to the plant material, steam and other gaseous materials may be produced as water and other components of the plant material are vaporized due to the increase in temperature. The plant material may be heated by various means, such as electrical means, pumped heated fluid, or pumped heated air, by way of example only. The region of the compartment that is being heated may be the same region of the compartment in which the plant material is first placed in the apparatus 101.

In one embodiment, the plant material is heated in two stages. In the first stage, the plant material is heated to temperatures in the range of 210° C. to 230° C. for a first defined period of time ranging between 18 and 25 hours. Following the first period of time, the plant material is heated to temperatures in the temperature range of 170° C. to 190° C. for a second defined period of time ranging between 18 and 25 hours.

It will be appreciated by those skilled in the art that different temperatures, times and sequences may be used in the heating process of the present invention.

During the process described above, the pressure in the compartment may be decreased to produce a negative vacuum state. In one embodiment, the pressure in the compartment may be kept at a pressure between 650 and 750 Torr. It will be appreciated by one of skill in the art that other negative pressure ranges may be used in the method of the present invention.

In one embodiment of the method of the present invention, the pressure in the compartment may reduced after heating the plant material for a time in the range of 19 to 22 hours, although it will be appreciated that the reduction in pressure may occur at other times during the process.

In one embodiment, once the negative pressure environment has been created in the compartment, it is maintained until the end of the method. In other embodiments of the method, the negative pressure may not be maintained until the end of the method, or may be applied intermittently during the method.

The vacuum negative pressure in the compartment may assist in the expansion of cells in the plant material and outflow of fluid from the cells. This may enhance the extraction of active ingredients from the plant material, and may also assist in the removal or extraction of unwanted chemicals or substances from the plant material as waste material. In the vacuum negative pressure environment, the cell structure of the plant material may become less dense, which may enhance the vaporization of fluid in the plant material.

Due to being heated, the evaporate may rise to the top 105 of the compartment of apparatus 101. The top of the compartment of apparatus 101 may be the region of the compartment which is being cooled. Such cooling may be provided by various sources, such as electrical means, coolant, pumped cooled fluid, pumped cooled air or cooling fan, by way of example only. In FIG. 1, a cooling fan, 104, is depicted. The cooling may be generated in such a way that the inward-facing surface 106 of the top of such compartment is cooled. The evaporate thus may condense by cooling on, or in close proximity to, the inner-facing surface, and the resulting condensate may thus be collected against such inward-facing surface.

In one embodiment, the cooling process is commenced in a time period between 19 and 22 hours following commencement of the heating process. It will be appreciated that in other embodiments of the invention, the cooling process may be commenced at different times. In other embodiments of the invention, the cooling may not be maintained until the end of the method, and cooling may be applied intermittently throughout the method.

In one embodiment, the cooling process is commenced in a time period between 3 and 5 hours following commencement of the 2nd heating process, and is continued until the end of the heating process. It will be appreciated that in other embodiments of the invention, the cooling process may be commenced at different times. In other embodiments of the invention, the cooling may not be maintained until the end of the heating process, and cooling may be applied intermittently throughout the heating process.

In one embodiment, the inner-facing surface may be shaped such that the condensate collected thereon will collect or move toward a certain location on such surface. Such location would preferably be located where, when the condensate forms droplets, and the droplets fall off the inner-facing surface due to gravity, the droplets would fall into a collection compartment 103 located below such location. In one embodiment, the inner-facing surface is a convex shape with the apex at the lowest point of the inner-facing surface, such that the condensate will collect toward the centre of the inner-facing surface. In such an embodiment, the collection compartment 103 would be located below the centre of the inner-facing surface, in order to maximize collection of the droplets of condensate as such droplets fall from the inner-facing surface. Although a convex shape for the inner-facing surface has been described in the present embodiment, it will be appreciated by those skilled in the art that other shapes for the inner-facing surface may also accomplish the desired effect of directing droplets toward a certain location from which they will ultimately fall into the collection compartment 103, such as an inverted pyramid with the apex at the lowest point of the inner-facing surface, for example, or other shapes in which droplets are encouraged to collect in a particular location, including shapes with multiple low points on the inner-facing surface. If an inner-facing surface is used with multiple low points, it will be appreciated that the collection compartment 103 would preferably be situated such that droplets from each low point would fall into the collection compartment 103, or multiple collection compartments could be used to collect droplets from each low point on the inner-facing surface.

After completion of the above-described method, the collection compartment 103 may be removed. The liquid contained therein may contain materials extracted from the plant material 102. In one embodiment, the plant material is *cannabis*, and the liquid collected may contain full-spectrum cannabinoids, cannabinoids, essential oils, alkanes, nitrogen-containing compounds, amino acids, sugar, aldehydes, alcohols, ketones, flavonoids, glycosides, vitamins and water from the body of *cannabis*. This may be detected by a certain detection method using a liquid chromatograph or a high-resolution mass spectrometer.

In one embodiment, this liquid collected in the collection compartment 103 may be stored separately and at room temperature. In one embodiment, waste materials may be collected outside of the collection compartment, for example, at the bottom of apparatus 101.

Figure 2:
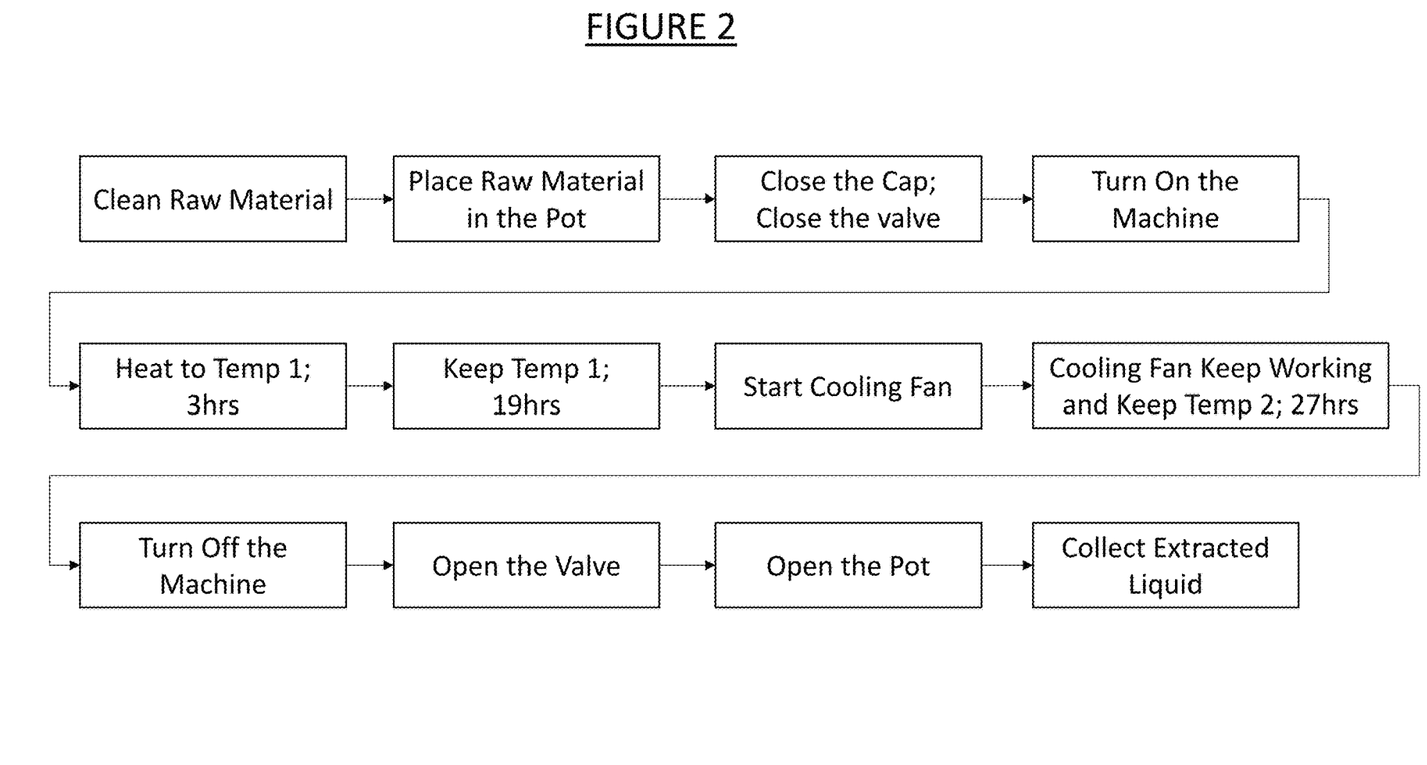
FIG. 2 is a process flow chart showing different steps in a method of extraction of ingredients from plant material.
Figure 3:
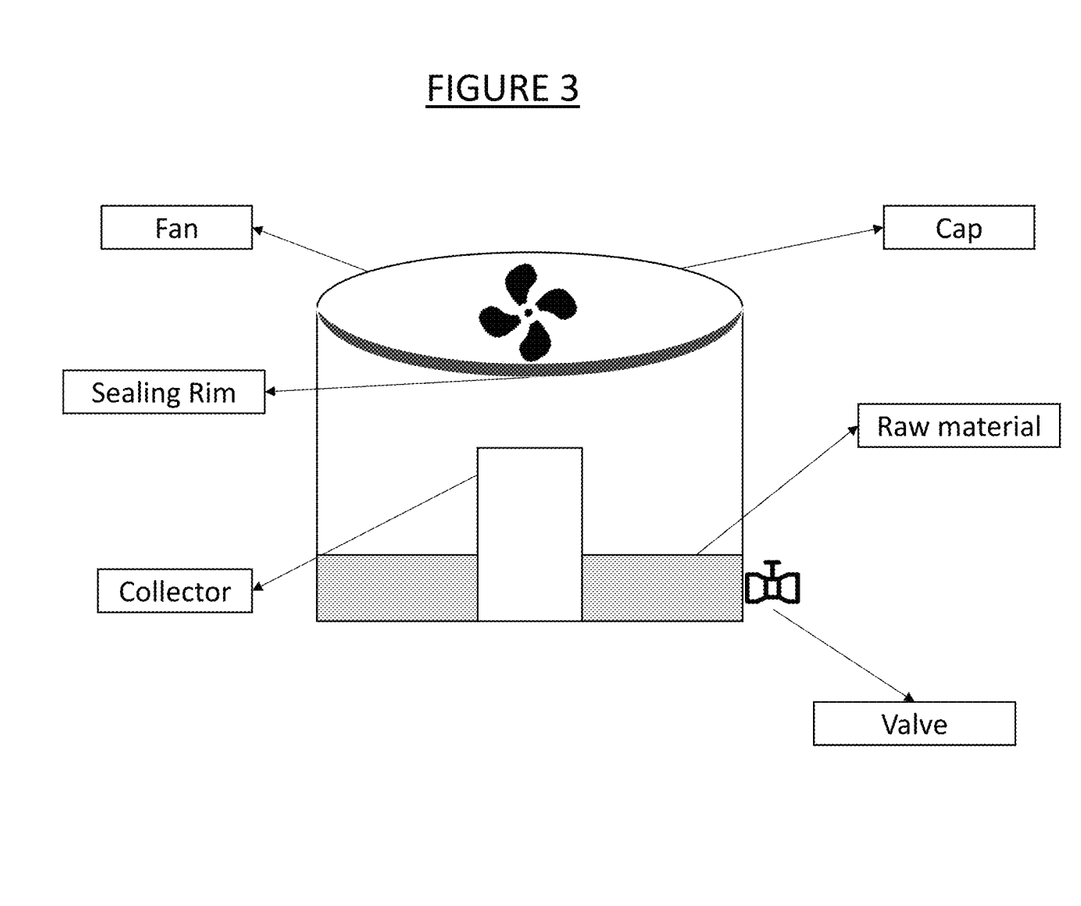
FIG. 3 is a schematic diagram showing an apparatus to be used in a method of the invention.

FIG. 2 shows a flow chart setting out an embodiment of the method of the invention. FIGS. 3 through 7 show a representative apparatus depicting an embodiment of a method of the invention, along with corresponding steps from the flow chart of FIG. 2. It will be appreciated that some of the steps shown in FIGS. 2 through 7 are similar or identical to steps described above, and these Figures may be used to further expand on, or clarify, the embodiments already described. Names of parts used in FIG. 3 may be used herein to refer to those parts in the description.

Figure 4:
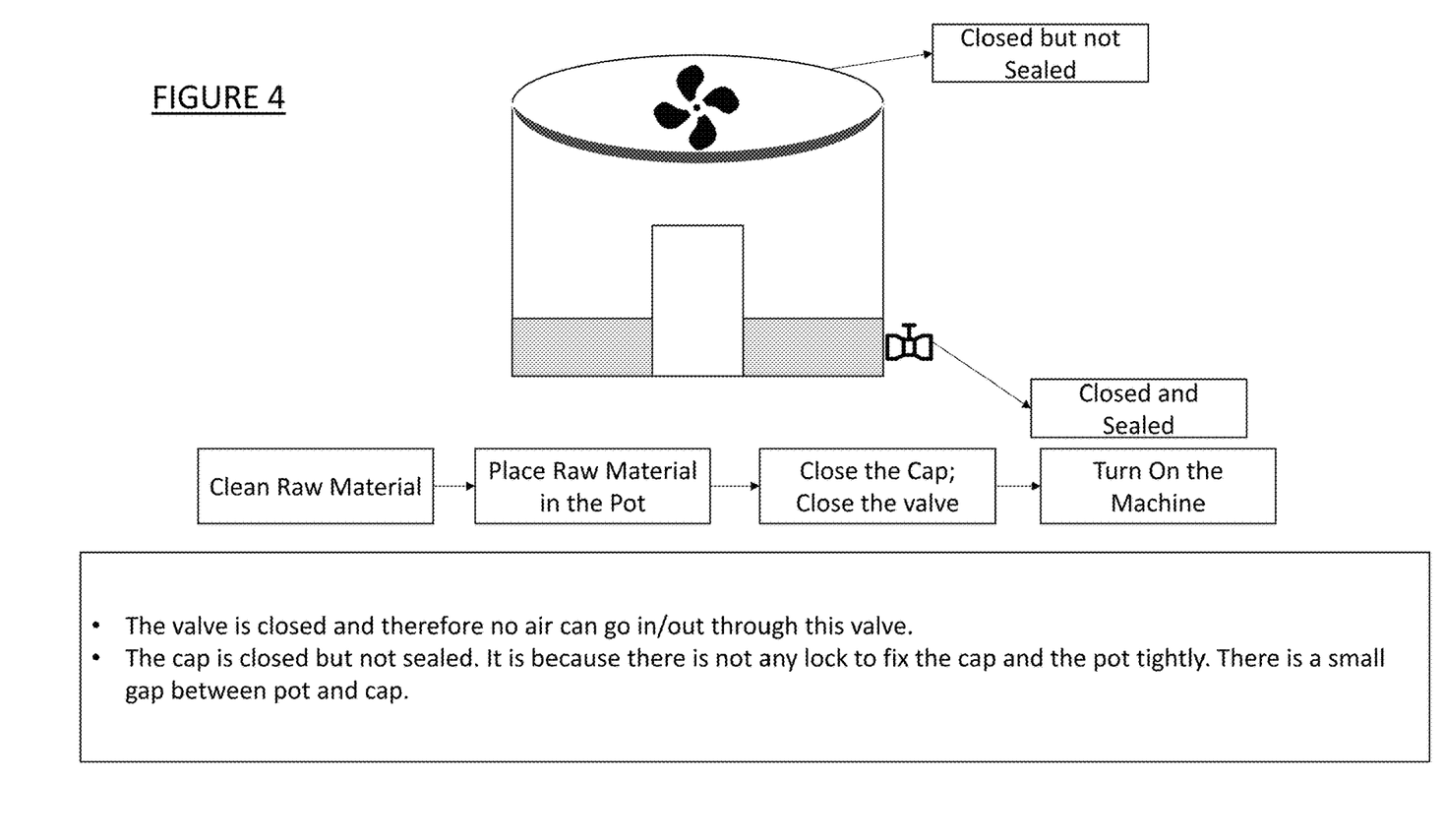
FIG. 4 is a schematic diagram showing and describing steps in a method of the invention.

With reference to FIG. 4, initial steps of an embodiment of a method of the invention are depicted. Raw plant material is first, optionally, cleaned, and then placed inside the apparatus. The top, or cap, of the apparatus is then closed, but may not be sealed. A valve on the apparatus is then closed and sealed. In one embodiment of the invention, a small gap may remain between a top edge of the apparatus and the cap of the apparatus. The apparatus may then be turned on.

Figure 5:
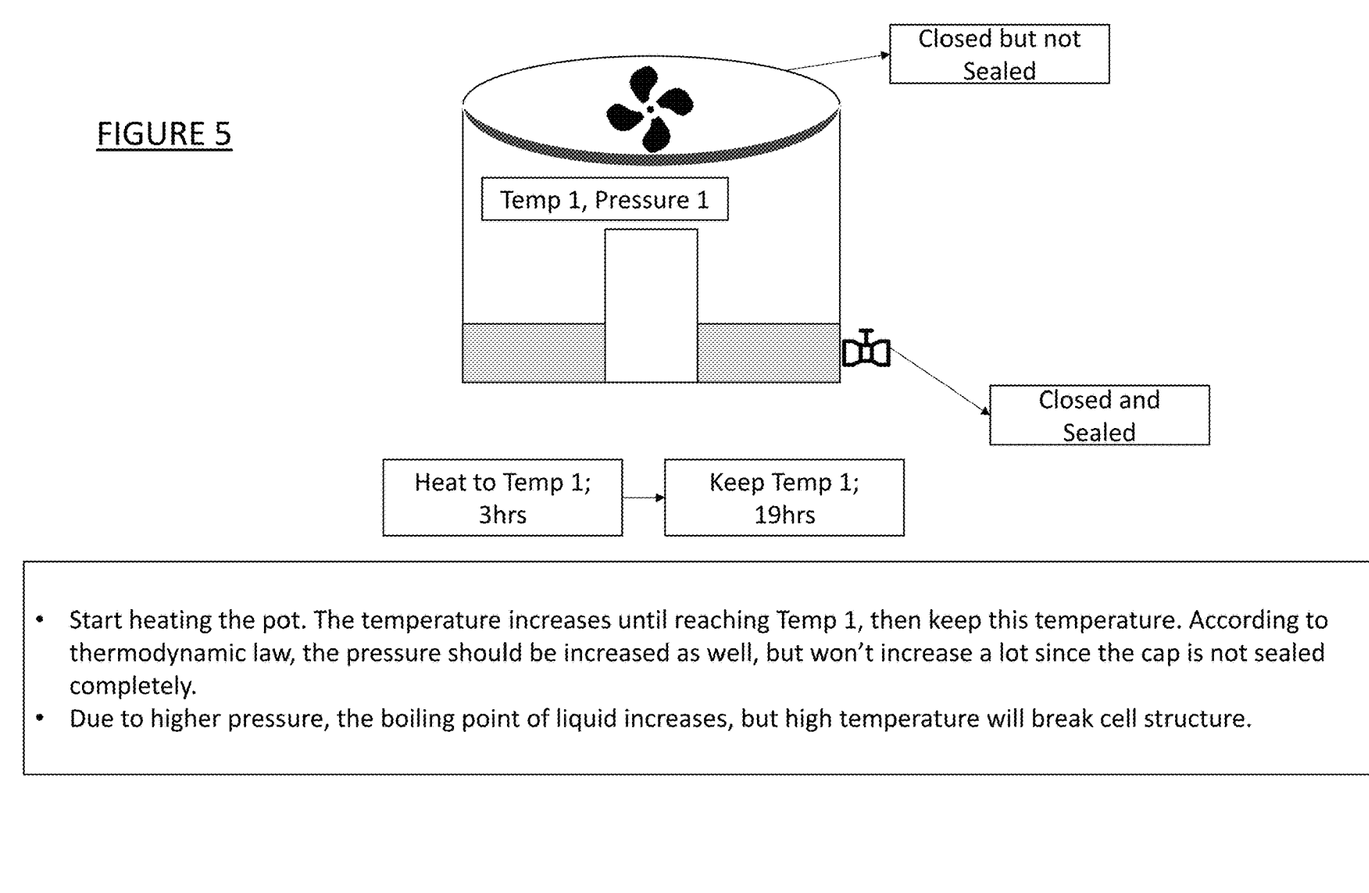
FIG. 5 is a schematic diagram showing and describing further steps in a method of the invention.

FIG. 5 shows further steps of an embodiment of a method of the invention. The interior of the apparatus is heated to a first temperature. In some embodiments of the method of the invention, it may take 3 hours of heating for the temperature within the apparatus to reach the first temperature. That first temperature may then be maintained for a first period of time. In some embodiments, that first period of time may be 19 hours, though it will be appreciated that other lengths of time may be used. This increase in temperature may cause an increase in internal pressure in the apparatus, though this pressure increase may not be significant since the cap of the apparatus in this embodiment may not be sealed at this time. Due to this higher pressure, the boiling point of liquid may increase as well. The higher temperature may assist in breaking down cell structure of the plant material in the apparatus, which may assist in extracting materials from the plant material.

Figure 6:
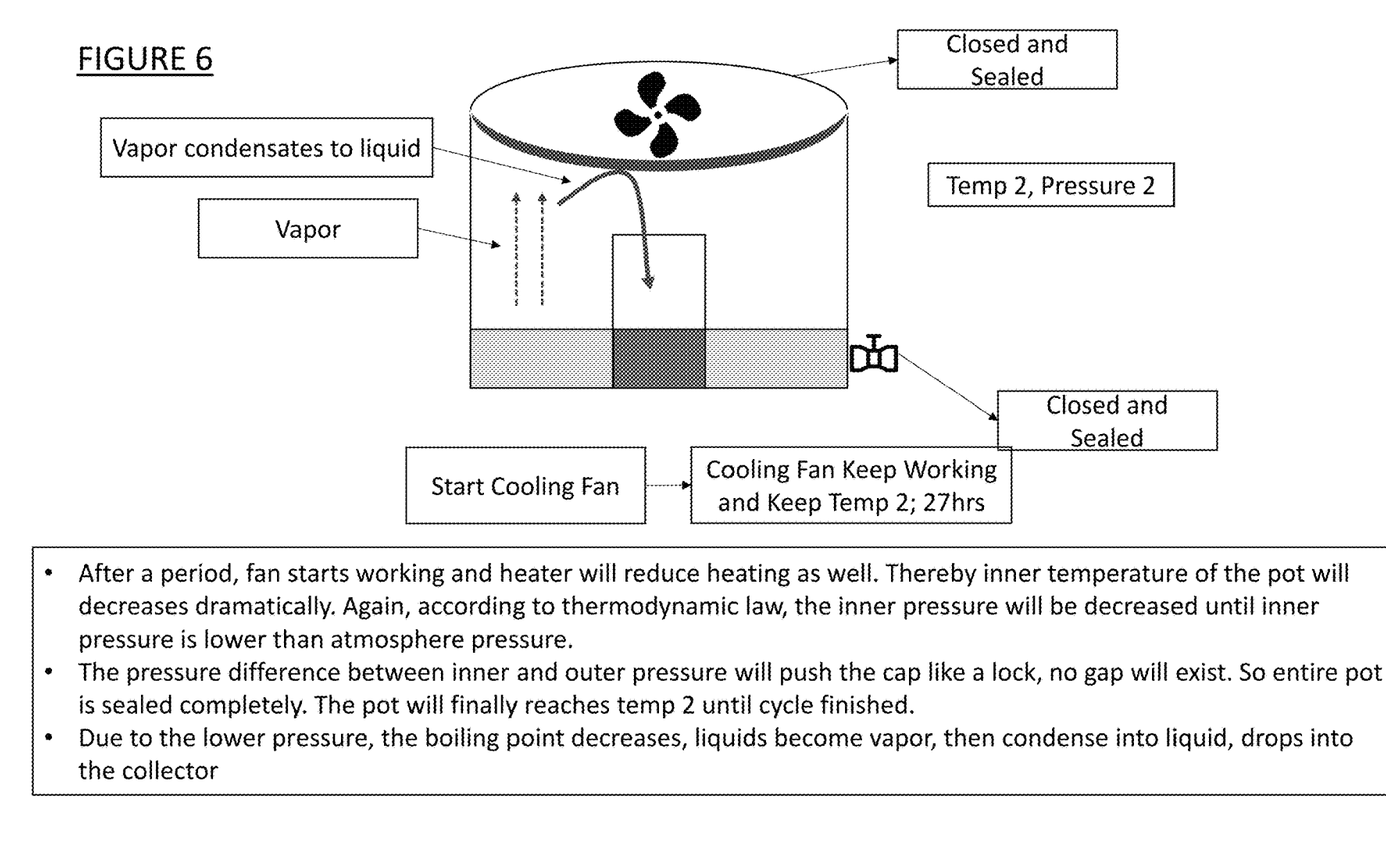
FIG. 6 is a schematic diagram showing and describing further steps in a method of the invention.

FIG. 6 shows further steps in an embodiment of the invention. After maintaining the first temperature for the first period of time, a cooling fan, or other cooling method, may be operated to reduce the temperature within the apparatus. The heat supplied by the heating method may also be decreased or ceased. Due to this cooling, the inner temperature within the apparatus may be decreased, and the pressure inside the apparatus may be decreased. Once the pressure inside the apparatus is less than atmospheric pressure outside the apparatus, the cap of the apparatus may be sealed in place by vacuum pressure, thus sealing the inside of the apparatus. The temperature inside the apparatus may reach a second temperature due to the cooling, and this second temperature may be maintained for a second period of time. Due to the lower pressure inside the apparatus, the boiling point of liquids may decrease, liquids may therefore become vapor, may then condense, as show in FIG. 6, and then the condensate may drop into a collector within the apparatus. It will be appreciated that the weight of the cap may be varied to assist with sealably closing, or that the cap may be spring loaded, or biased in some way toward creating the seal described herein.

Figure 7:
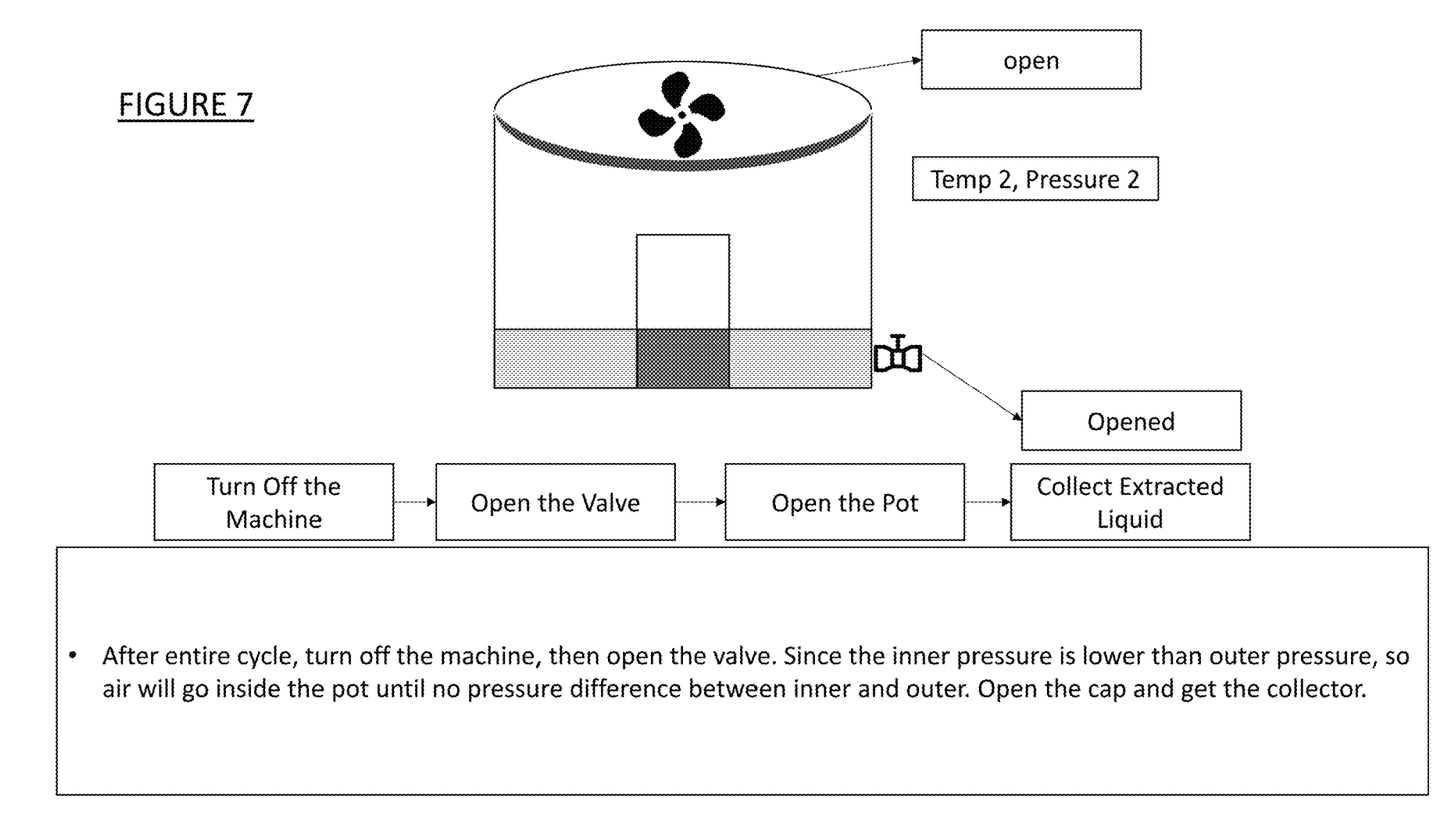
FIG. 7 is a schematic diagram showing and describing further steps in a method of the invention.

Referring to FIG. 7, once the cycle described has completed, the apparatus may be turned off, and the valve may be opened. By opening the valve, air outside the apparatus is allowed into the apparatus and the inner pressure of the apparatus may equalize with the atmospheric pressure outside the apparatus. The cap may then be opened, and the collector, and/or the collected condensate (extracted liquid), may be retrieved.

In some embodiments, after several nuclear magnetic resonance (NMR600 Hz) tests, the semi-high peak width of the extracted liquid of this invention is within the range of 39-50 hz. This molecule size is half the size of normal small molecule water (80-100 hz) and is more easily absorbed in the body.

The present invention provides, in accordance with some embodiments, a solution that is simple, convenient, quick, and which extracts full composition, high concentration and stable outputs so that the extracts can be more easily absorbed in the body.

Due to the methods described herein, there are at least four main features of the product derived from the extraction methods of the invention.

As a first main feature, the end product may be considered to be "full-spectrum", in that almost all of the components within the plant material cells can be extracted. In the example of *cannabis*, liquid collected may contain full-spectrum cannabinoids, cannabinoids, essential oils, alkanes, nitrogen-containing compounds, amino acids, sugar, aldehydes, alcohols, ketones, flavonoids, glycosides, vitamins and water from the body of *cannabis*.

As a second main feature, some extracted liquid may be anti-oxidant. This may assist with storage of the extracted liquid.

As a third main feature, the end product may be considered to be organic, due to the method of the invention described herein and not using any chemical additive in the extraction process.

As a fourth main feature, the end product may be easily absorbed. This may be due to the smaller dimension of the particles in the extracted materials. The end product also may be soluble in water. With some plant material, for example, *cannabis*, some extraction methods result in oils as the end product, which are insoluble in water. Materials extracted from *cannabis* in certain of the embodiments of the methods described herein may be water-soluble. They may also be fat soluble. They may show improved mixing uniformity. They may show improved stability. They may show improved multiphase liquid mixing uniformity. They may be water resistant.

In one embodiment of the invention, the *cannabis* product of this invention is an ultra small molecule. A nuclear magnetic resonance (NMR) NMR test shows that the product has a small molecular mass of 49 HZ, being the same as the size of 5 to 6 water molecular clusters. Because of the size of this ultra small molecule, this can solve some of the problems referenced above.

It will be appreciated that it may be that the methods of this invention may be employed and developed in jurisdictions in which such methods are legal, with respect to the plant material being used. For example, with respect to *cannabis*, methods described herein may not be legal in some countries, while it would be legal in others, such as Canada.

It will be appreciated that materials extracted from plant material using the methods of the invention described herein may be used in various industries and products relating thereto, including the beverage industry, cosmetic industry and food industry.

The approach of this invention is physical; the special physical phenomenon of molecular bond breaking caused by vacuum negative pressure makes liquid change from macromolecular groups to smaller molecular groups, which increases the contact interface between molecules, which is extremely conducive to the polymerization or decomposition of various liquid phase liquids. The method of the present invention breaks molecular bonds, making the length of the molecular bond of the heterogeneous liquid similar in length, which promotes the polymerization of heterogeneous liquid that may be otherwise difficult to fuse.

The method of the present invention has high extraction efficiency, low extraction cost and stable outputs. This method can be applied to a variety of plant products for extraction of materials therefrom. This method extracts whole ingredients in a concentrated condensate, improving the stability of the ingredients extracted from the plant materials, and minimizing waste of ingredients in the extraction process.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the relevant patent office and the public generally, and especially the scientist, engineers and practitioners in the art who are not familiar with patent or legal terms or phraseology, to determine quickly from a cursory inspection the nature and essence of the technical disclosure of the application.

EXAMPLES

Below are several provided examples intended to illustrate specific embodiments of this disclosure. These examples are illustrative and not intended to be limiting of the broader scope of the disclosure.

Example 1: An embodiment of the method of the invention was employed as set forth in this example.

A 4.3 kg sample of *cannabis*-blueberry type was placed within an apparatus as used in the method described above. The sample of *cannabis* was not pre-treated. At the start of the extraction process, the temperature of the sample was measured to be 17° C.

Next, in a first stage of heating, the *cannabis* was heated to a temperature of 230° C. during a period of 24 hours and 20 minutes. Next, in a second stage, the temperature of the sample was heated to 190° C. during a period of 22 hours and 10 minutes.

Following the second stage, the liquid extracted from the material was collected. 1.9 kg of liquid were collected. The appearance of the liquid was recorded as light yellow. It was reported as having a strong *cannabis* taste. A small amount of an oil-like substance was noted floating on the top of the sample.

The solid sample remaining following the extraction of the liquid from the material was reported as still partially wet. 1.75 kg of solid sample remained following extraction of the liquid therefrom. The taste was reported as being the same as the taste of the liquid sample. The appearance was recorded as being dark green where the sample was dry, and yellow where the sample was partially wet.

Example 2: Various chemical analyses were performed on a 50 mL sample of liquid extracted from medical *cannabis* according to an embodiment of the method of this invention. The tests used, and a summary of the Certificate of Analysis results, are listed below.

| Test | Method | Specification | Result |
|---|---|---|---|
| Abamectin | CHM.016 | <10 ppb | <10 ppb |
| Ethoprophos | CHM.016 | <10 ppb | <10 ppb |
| Etofenprox | CHM.016 | <10 ppb | <10 ppb |
| Acephate | CHM.016 | <10 ppb | <10 ppb |
| Acetamiprid | CHM.016 | <10 ppb | <10 ppb |
| Etoxazole | CHM.016 | <10 ppb | <10 ppb |
| Acequinocyl | CHM.016 | <10 ppb | <10 ppb |
| Aldicarb | CHM.016 | <10 ppb | <10 ppb |
| Allethrin | CHM.016 | <10 ppb | <10 ppb |
| Etridiazol | CHM.016 | <10 ppb | <10 ppb |
| Azadirachtin | CHM.016 | <10 ppb | <10 ppb |
| Fenoxycarb | CHM.016 | <10 ppb | <10 ppb |
| Azoxystrobin | CHM.016 | <10 ppb | <10 ppb |
| Benzovindiflupyr | CHM.016 | <10 ppb | <10 ppb |
| Fenpyroximate | CHM.016 | <10 ppb | <10 ppb |
| Bifenazate | CHM.016 | <10 ppb | <10 ppb |
| Bifenthrin | CHM.016 | <10 ppb | <10 ppb |
| Fensulfothion | CHM.016 | <10 ppb | <10 ppb |
| Boscalid | CHM.016 | <10 ppb | <10 ppb |
| Buprofezin | CHM.016 | <10 ppb | <10 ppb |
| Carbaryl | CHM.016 | <10 ppb | <10 ppb |
| Dimethomorph | CHM.016 | <10 ppb | <10 ppb |
| Fenthion | CHM.016 | <10 ppb | <10 ppb |
| Carbofuran | CHM.016 | <10 ppb | <10 ppb |
| Fenvalerate | CHM.016 | <200 ppb | <200 ppb |
| Chlorantraniliprole | CHM.016 | <10 ppb | <10 ppb |
| Chlorphenapyr | CHM.016 | <50 ppb | <50 ppb |
| Chlorpyrifos | CHM.016 | <10 ppb | <10 ppb |
| Clofentezine | CHM.016 | <10 ppb | <10 ppb |
| Clothianidin | CHM.016 | <10 ppb | <10 ppb |
| Coumaphos | CHM.016 | <10 ppb | <10 ppb |
| Cyantranilipole | CHM.016 | <10 ppb | <10 ppb |
| Cyfluthrin | CHM.016 | <50 ppb | <50 ppb |
| Cypermethrin | CHM.016 | <10 ppb | <10 ppb |
| Cyprodinil | CHM.016 | <10 ppb | <10 ppb |
| Daminozide | CHM.016 | <200 ppb | <200 ppb |
| Deltamethrin | CHM.016 | <10 ppb | <10 ppb |
| Diazinon | CHM.016 | <10 ppb | <10 ppb |
| Dichlorvos | CHM.016 | <10 ppb | <10 ppb |
| Dimethoate | CHM.016 | <10 ppb | <10 ppb |
| Dinotefuran | CHM.016 | <10 ppb | <10 ppb |
| Dodemorph | CHM.016 | <10 ppb | <10 ppb |
| Endosulfan-alpha | CHM.016 | <100 ppb | <100 ppb |
| Endosulfan-beta | CHM.016 | <500 ppb | <500 ppb |
| Endosulfan sulfate | CHM.016 | <50 ppb | <50 ppb |
| Piperonyl butoxide | CHM.016 | <10 ppb | <10 ppb |
| Pirimicarb | CHM.016 | <10 ppb | <10 ppb |
| Prallethrin | CHM.016 | <10 ppb | <10 ppb |
| Propiconazole | CHM.016 | <10 ppb | <10 ppb |
| Propoxur | CHM.016 | <10 ppb | <10 ppb |
| Pyraclostrobin | CHM.016 | <10 ppb | <10 ppb |
| Pyrethrins | CHM.016 | <10 ppb | <10 ppb |
| Pyridaben | CHM.016 | <10 ppb | <10 ppb |
| Quintozene | CHM.016 | <10 ppb | <10 ppb |
| Resmethrin | CHM.016 | <50 ppb | <50 ppb |
| Spinetoram | CHM.016 | <10 ppb | <10 ppb |
| Spinosad | CHM.016 | <10 ppb | <10 ppb |
| Spirodiclofen | CHM.016 | <10 ppb | <10 ppb |
| Spiromesifen | CHM.016 | <10 ppb | <10 ppb |

| Test | Method | Specification | Result |
|---|---|---|---|
| Spirotetramat | CHM.016 | <10 ppb | <10 ppb |
| Fipronil | CHM.016 | <10 ppb | <10 ppb |
| Spiroxamine | CHM.016 | <10 ppb | <10 ppb |
| Tebuconazole | CHM.016 | <10 ppb | <10 ppb |
| Flonicamid | CHM.016 | <10 ppb | <10 ppb |
| Tebufenozide | CHM.016 | <10 ppb | <10 ppb |
| Fludioxonil | CHM.016 | <10 ppb | <10 ppb |
| Teflubenzuron | CHM.016 | <10 ppb | <10 ppb |
| Tetrachlorvinphos | CHM.016 | <10 ppb | <10 ppb |
| Tetramethrin | CHM.016 | <10 ppb | <10 ppb |
| Fluopyram | CHM.016 | <10 ppb | <10 ppb |
| Thiacloprid | CHM.016 | <10 ppb | <10 ppb |
| Thiamethoxam | CHM.016 | <10 ppb | <10 ppb |
| Hexythiazox | CHM.016 | <10 ppb | <10 ppb |
| Thiophanate-methyl | CHM.016 | <50 ppb | <50 ppb |
| Trifloxystrobin | CHM.016 | <10 ppb | <10 ppb |
| Imazalil | CHM.016 | <10 ppb | <10 ppb |
| Imidacloprid | CHM.016 | <10 ppb | <10 ppb |
| Iprodione | CHM.016 | <10 ppb | <10 ppb |
| Kinoprene | CHM.016 | <50 ppb | <50 ppb |
| Kresoxim-methyl | CHM.016 | <10 ppb | <10 ppb |
| Malathion | CHM.016 | <10 ppb | <10 ppb |
| Metalaxyl | CHM.016 | <10 ppb | <10 ppb |
| Methiocarb | CHM.016 | <10 ppb | <10 ppb |
| Methomyl | CHM.016 | <10 ppb | <10 ppb |
| Methoprene | CHM.016 | <50 ppb | <50 ppb |
| Methyl parathion | CHM.016 | <10 ppb | <10 ppb |
| Mevinphos | CHM.016 | <10 ppb | <10 ppb |
| MGK-264 | CHM.016 | <10 ppb | <10 ppb |
| Myclobutanil | CHM.016 | <10 ppb | <10 ppb |
| Naled | CHM.016 | <500 ppb | <500 ppb |
| Novaluron | CHM.016 | <10 ppb | <10 ppb |
| Oxamyl | CHM.016 | <10 ppb | <10 ppb |
| Paclobutrazol | CHM.016 | <10 ppb | <10 ppb |
| Permethrin | CHM.016 | <10 ppb | <10 ppb |
| Phenothrin | CHM.016 | <10 ppb | <10 ppb |
| Phosmet | CHM.016 | <10 ppb | <10 ppb |
| Delta-9-tetrahydrocannabinol/ Delta-9-tetrahydrocannabinol acid/Total Delta-9-Tetrahydrocannabinol | EXPTM 613, Rev. 02 | Report % w/v | THC: 0.012% w/v THCA: 0.000% w/v Total THC: 0.012% w/v AS IS |
| Cannabidiol/Cannabidiol Acid/Total Cannabidiol | EXPTM 613, Rev. 02 | Report % w/v | CBD: Not Detected CBDA: Not Detected Total CBD: Not Detected |
| Cannabinol | EXPTM 613, Rev. 02 | Report % w/v | 0.000% w/v |
| CBC/CBCA | EXPTM 613, Rev. 02 | Report % w/v | CBC: 0.000% w/v CBCA: Not Detected |
| CBC/CBCA | EXPTM 613, Rev. 02 | Report % w/v | CBG: 0.000% w/v CBGA: 0.000% w/v |
| Terpene Profile (alpha-Pinene, Camphene, (−)-beta-Pinene, beta-Myrcene, delta-3-carene) | EXPTM 665, Rev. 01 | Report | alpha-pinene: Not Detected Camphene: 0.0000% w/w Beta-Pinene: Not Detected Beta-Myrcene: 0.0001% w/w delta-3-carene: Not Detected |
| Terpene Profile (alpha-Terpinene, p-Cymene, d-Limonene, Ocimene, gama-Terpinene) | EXPTM 665, Rev. 01 | Report | alpha-Terpinene: Not Detected p-Cymene: Not Detected d-Limonene: 0.0002% w/w Ocimene: Not Detected gama-Terpinene: Not Detected |
| Terpene Profile (Terpinolene, Linalool, Isopulegol, Geraniol, beta-Caryophyllene) | EXPTM 665, Rev. 01 | Report | Terpinolene: Not Detected Linalool: 0.0033% w/w Isopulegol: Not Detected Geraniol: 0.0004% w/w beta-Caryophyllene: 0.0057% w/w |
| Terpene Profile (alpha-Humulene, Nerolidol, Guaiol, alpha-Bisabolol, alpha-Terpineol) | EXPTM 665, Rev. 01 | Report | alpha-Humulene: 0.0021% w/w Nerolidol: 0.0011% w/w Guaiol: 0.0002% w/w alpha-Bisabolol: 0.0010% w/w alpha-Terpineol: 0.0015% w/w |
| Assay: Cadmium | Ph. Eur. 2.4.27 | <0.5 ppm | <0.0004 ppm |
| Assay: Lead | Ph. Eur. 2.4.27 | <0.5 ppm | <0.0025 ppm |
| Assay: Arsenic | Ph. Eur. 2.4.27 | <1.5 ppm | <0.0033 ppm |
| Assay: Total Mercury | Ph. Eur. 2.4.27 | <1.5 ppm | <0.0008 ppm |
| Aflatoxins (B1 + B2 + G1 + G2) | AOAC 991.31 | <4 ppb | Not Detected (<4 ppb) |

-continued

| Test | Method | Specification | Result |
|---|---|---|---|
| Aflatoxins B1 | AOAC 991.31 | <2 ppb | Not Detected (<2 ppb) |
| Foreign Matter | Microscopic | The sample is visually inspected to ensure it is essentially free of individual stem (>1.5 cm), hair, insects and other solids. | Conforms |
| Total Aerobic Plate Count | Current EP <2.6.12> | ≤1 × 10$^5$ cfu/g | 1 × 10$^1$ cfu/g |
| Total Yeasts and Molds | Current EP <2.6.12> | ≤1 × 10$^4$ cfu/g | <10 cfu/g |
| Bile Tolerant Gram Negative Bacteria | Current EP <2.6.31> | ≤1 × 10$^4$ cfu/g | <10 cfu/g |
| *E. coli* | Current EP <2.6.31> | Absent (1 g) | No Growth Detected |
| *Salmonella* spp | Current EP <2.6.31> | Absent (25 g) | No Growth Detected |
| *Pseudomonas aeruginosa* | Current EP <2.6.13> | Absent | No Growth Detected |
| *Staphylococcus aureus* | Current EP <2.6.13> | Absent | No Growth Detected |

Example 3: Various chemical analyses were performed on a sample of liquid extracted from *cannabis* according to an embodiment of the method of this invention. The tests used, and a summary of the Certificate of Analysis results, are listed below.

| Test | Method | Specification | Result |
|---|---|---|---|
| Total Aerobic Plate Count | Ph. Eur. 2.6.12 | Report | 9.5 × 10$^5$ cfu/ml |
| *E. coli* | Ph. Eur. 2.6.31 | Report | No growth detected. |
| *Salmonella* spp | Ph. Eur. 2.6.31 | Report | None detected. |

Example 4: Various chemical analyses were performed on a sample of liquid extracted from plant material consisting of carrot according to an embodiment of the method of this invention. The tests used, and a summary of the Certificate of Analysis results, are listed below.

| Test | Method | Specification | Result |
|---|---|---|---|
| Ash | TR017 | Report | 0.038% |
| Salt % | QD300 | Report | <0.1% |
| Fatty Acid Profile | TR00G | Report | Total Fat: 0%<br>Total Fatty Acids: 0%<br>Total saturated fatty acid: 0%<br>Cis-Monounsaturated fatty acids: 0%<br>Cis-polyunsaturated fatty acids: 0%<br>Total unsaturated fatty acids: 0%<br>Total trans fatty acids: 0%<br>Omega-3 fatty acids: 0%<br>Omega-6 fatty acids: 0% |
| Moisture Content | QD153 (Karl Fischer) | Report | 99.4% |
| Vitamin A | TR01B (Retinol) | Report | <20 IU/100 g |
| Vitamin C | TR00J | Report | 0.0841 mg/100 g |
| Peroxide Value | Current USP | Report | 0.00 (no blue colour observed on the addition of starch) |
| *E coli*, Coliform | MFHPB-34 | Report | Coliforms: <10 cfu/g<br>*E. coli*: <10 cfu/g |
| *Salmonella* | MFLP-49 | Report | *Salmonella*: Not detected per 25 g |
| ACC total plate count | MFHPB-18 | Report | <10 cfu/g |

Although examples of this invention have been shown and described above, it is understood that these are just examples, and cannot be understood as restrictions of this invention, and that technicians in the field may change, or modify the above embodiments within the scope of the invention. In particular, any other solution may be adopted such as the heating system, the cooling system and processing time and temperature to achieve the same object as this invention, but all such design changes belong to the scope of this invention. Accordingly, the scope of the invention is to

The invention claimed is:

1. A method for extracting chemicals from plant material comprising one or more plants from the plant genus *Cannabis*, such method comprising the following steps:
   a. heating the plant material within an apparatus in which a vacuum pressure is applied on the plant material within the apparatus;
   b. cooling the apparatus such that evaporate produced from the heated plant material is cooled and condenses; and
   c. collecting the condensed evaporate from the plant material;
   wherein the space within the apparatus into which the plant material is placed is cleaned and disinfected prior to the plant material being placed therein;
   wherein the plant material is washed with water and pasteurized before being placed within the apparatus;
   wherein the vacuum pressure on the plant material within the apparatus is within the range of 650 to 750 Torr;
   wherein the vacuum pressure is applied after heating the plant material; and
   wherein the vacuum pressure is applied intermittently.

2. The method of claim 1, wherein the cooling is applied within 3 to 5 hours after heating the plant material has commenced.

3. The method of claim 2, wherein the cooling is applied continually after the heating of the plant material has ended.

4. The method of claim 2, wherein the cooling is applied intermittently after the heating of the plant material.

5. The method of claim 4, wherein the plant material is heated for a period of time between 19 and 22 hours in length.

6. The method of claim 5, wherein the plant material is cooled for a period of 27 hours after heating.

7. The method of claim 1, the condensed evaporate having a molecular mass corresponding to a semi-high peak width produced in the range of 39-50 Hz in a nuclear magnetic resonance test.

* * * * *